United States Patent [19]

Smith, Jr.

[11] 4,306,068

[45] Dec. 15, 1981

[54] PROCESS FOR SEPARATING PRIMARY AND SECONDARY AMINES

[75] Inventor: Lawrence A. Smith, Jr., Houston, Tex.

[73] Assignee: Chemical Research and Licensing Company, Houston, Tex.

[21] Appl. No.: 889,360

[22] Filed: Mar. 23, 1978

[51] Int. Cl.$^3$ .................. C07D 295/02; C07C 85/26
[52] U.S. Cl. .................... 546/184; 564/216; 564/305; 564/462; 564/499
[58] Field of Search ............ 260/293.51, 582, 583 N; 546/184; 564/305, 462, 499, 216

[56] References Cited

U.S. PATENT DOCUMENTS

| | | | |
|---|---|---|---|
| 1,898,461 | 2/1933 | Nicodemus et al. | 260/583 N |
| 3,331,875 | 7/1967 | Strickland | 260/582 |
| 3,594,421 | 7/1971 | Kmiecik | 260/582 |
| 4,174,351 | 11/1979 | Shoffner | 564/499 |

FOREIGN PATENT DOCUMENTS 702985  1/1954  United Kingdom .

OTHER PUBLICATIONS

Morrison, R., et al., *Organic Chemistry*, Allyn and Bacon, Boston, 1979, pp. 858, 859, 865-870.
March, J., *Advanced Organic Chemistry*, 2nd Ed., McGraw Hill, N.Y., 1977, pp. 188-190.
Ingold, C., *Structure and Mechanism in Organic Chemistry*, Cornell U. Press, Ithaca, N.Y., 1953, pp. 60-67.
Sprung, M., *Chem. Reviews*, 26, p. 305 (1940).
Patai, S. (Editor), *The Chemistry of the Carbon-Nitrogen Double Bond*, Interscience, London, 1970, p. 300.
Kekulé, A., et al., *Annalen der Chemie und Pharmacie*, 162, p. 142 (1872).
Layer, R., *Chem. Reviews*, 63, 489-510 (1963).
Beilstein, F., *Handbuch der Organischen Chemie*, 1st Supp., Springer Verlag, Berlin, 1934, vol. 19, p. 385.
Smith, P., The Chemistry of Open-Chain Organic Nitrogen Compounds, vol. I, W. A. Benjamin, New York, 1965, p. 294.
Pollack, R. M., et al., *J. Am. Chem. Soc.*, 94, 2534-2535 (1972).

*Primary Examiner*—Richard A. Schwartz
*Attorney, Agent, or Firm*—Kenneth H. Johnson

[57] ABSTRACT

A method for separating primary and secondary amines by contacting a mixture thereof with mesityl oxide, which forms acetone and an adduct with the primary amine. Acetone is removed to force the reaction. The reaction is particulary useful for separating close boiling amines. The primary amine adducts have high boiling points, thereby allowing the secondary amine to be recovered in high purity by distillation. The primary amine may also be recovered by hydrolyzing the adduct which produces the primary amine and acetone.

9 Claims, No Drawings

PROCESS FOR SEPARATING PRIMARY AND SECONDARY AMINES

BACKGROUND OF THE INVENTION

The present invention relates to a new reaction of mesityloxide with primary amines. More particularly, it relates to reaction of mesityl oxide with primary amines in admixture with other organic compounds, specifically secondary amines, to form high boiling adducts of the mesityl oxide and primary amine from which the secondary amine is readily separated in high purity.

The separation of primary amines from secondary amines is of commercial interest, but this separation is frequently complicated by their close boiling points and other physical and chemical properties. For example, piperidine (B.P. 106° C.) and n-amyl amine (B.P. 104° C.) are co-produced in some commercial processes. Piperidine is a valuable speciality chemical, which is commercially produced by the hydrogenation of pyridine, and sells for several dollars a kilogram. Hence, the separation and recovery of by-product piperidine would be highly beneficial. However, prior attempts to produce high purity piperidine from a mixture of piperidine and n-amyl amine have failed. The obvious approach of frictioning the by-product stream fails because the piperidine and n-amyl amine are so closely related in distillation properties that fractionation to high purity is impossible. They both form close boiling minimum azeotropes with water as well as close boiling maximum azeotropes with a number of alcohols including n-butyl, isobutyl and secondary butyl alcohol.

Several chemical reaction schemes have been proposed to separate piperidine and n-amyl amine. One process involves the reaction of the n-amyl anine with an aldehyde or ketone to form an "imine" which may be represented by the general reaction of

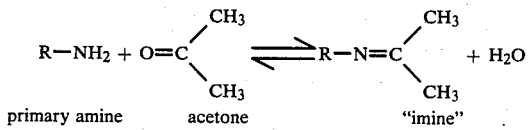

The secondary amines cannot form an imine. The reaction is reversible and the water must be removed to drive the reaction to completion. To achieve this result, high boiling ketones are employed with benzene to azeotrope the water from the reaction mixture. The piperidine can be fractionated from the reaction mixture after all of the n-amyl amine is reacted. This separation can be difficult, and this scheme is somewhat cumbersome.

SUMMARY OF THE INVENTION

Briefly stated, the present invention is the discovery of a new reaction of primary amines with mesityl oxide which provides a means of separating primary amines from other organic compounds in solution therewith, particularly, from secondary amines. In particular, one aspect of the present invention is the reaction of primary amines with mesityl oxide to form high boiling or solid adducts therewith in the presence of secondary amines and the removing of secondary amines from the reaction mixture.

Another aspect of the present invention is the method of reacting primary amines of the structure R—NH₂ with mesityl oxide to produce the imine compounds of the structure

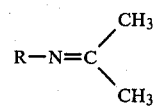

which is useful to produce acetone.

The nature of the reaction of mesityl oxide and primary amine is surprising. Unlike the reaction of ketones and primary amines, there is no water produced. However, acetone is produced as a by-product. The reaction may be depicted by the equation

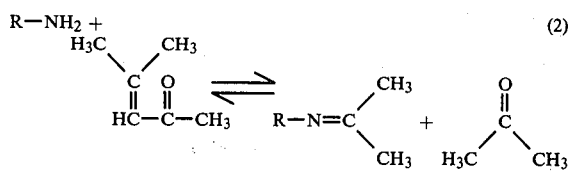

Although the reaction is reversible, it is easily carried out under such conditions to fractionate the acetone concurrently with the reaction and thereby drive the reaction to completion with relative ease.

The imine adduct,

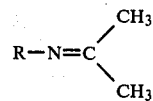

may be hydrolyzed to produce the primary amine and additional acetone.

The R is an aliphatic, olefinic or aromatic organic radical, preferably a hydrocarbon, including both cyclic and acylic aliphatic and olefinic radicals. Preferably R contains from 1 to 30 carbon atoms. The organic radical may contain various substituents such as the halogens (Br, Cl, I, F) which do not interfer with adduct reaction.

The process may be carried out continuously or batch wise. The reaction proceeds without catalysts and because of the desire to remove acetone, it is generally carried out at a temperature above the boiling point of acetone, however the reaction may be carried over a wide temperature range, for example, the range of −10° to 300° C. (under atmospheric pressure conditions). Preferably the temperature of the process will be from about 60° C. to 150° C.

The presence of water causes the primary amine-mesityl oxide adduct to hydrolyze to primary amine and acetone, however, the reaction of Eq 2 continues until the water in the system is removed. Hence, the presence of water presents no problem to the present invention.

Thus the present process is also an excellent method of dehydrating primary amines. The dehydration may be represented by:

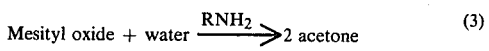

More specifically, the reaction when water is present is carried out as in Eq 2, with the concurrent removal of acetone. The reversable reaction of water with the adduct (Eq 1) is also in progress to produce an additional mol of acetone and primary amine. This continues until the water is exhausted, which would be indicated by a reduction in the amount of acetone to one mole per mole of mesityl oxide. The addition of mesityl oxide would be terminated unless the adduct rather than the primary amine were the desired product. In a continuous or batch process the primary amine would be recovered and the adduct recycled to water contaminated feed where it would be hydrolyzed and the dehydration repeated.

The present reaction may also be employed to selectively protect a primary amine function on a multifunctional organic compound by forming the adduct. The organic compound with adduct amine function can then undergo reaction of the other functional group or groups followed by regeneration of the amine function by hydrolysis of the adduct.

The mesityl oxide is preferably used in a substantially stoichiometric amount with the primary amine or in a slight excess.

SPECIFIC EMBODIMENTS

EXAMPLE 1

Twenty ml of mesityl oxide and 20 ml of a mixture of n-amyl amine and piperidine (60:40 mol) were added to a 50 ml flask equipped with a reflux condenser and a six inch distillation column packed with glass beads. This mixture was heated for about one hour. During this time the temperature in the flask rose from 45° to 123° C. A total of 17 ml of overhead was collected at overhead temperature of 30°–67° C. The over head product was identified as acetone. The n-amyl amine-mesityl oxide adduct, piperidine and unreacted n-amyl amine and mesityl oxide remained in the flask.

EXAMPLE 2

The same procedure as in Example 1 was carried out using cyclohexyl amine. 11.5 ml of acetone was collected over about 25 minutes at a pot temperature beginning at 47° C. to a final of 166° C. and over temperatures of 32° C. to 60° C.

EXAMPLE 3

The same procedure as in Example 1 was carried out using aniline. The reaction was continued for 50 minutes with the pot temperature beginning at 34° C. to 174° C. at termination and the overhead ranged from 31° C. to 62° C. over this same period. Eight ml of acetone was collected.

Examples 2 and 3 demonstrate the reaction of primary amines other than n-amyl amine with mesityl oxide, although aniline reacts very slowly.

N-butyl amine and formamide were evaluated in the same manner and were found to operate in the same manner.

In addition to mesityl oxide, crotonaldehyde, methyl vinyl ketone and diacetone alcohol were evaluated as the adducting agents. Crotonaldehyde and methyl vinyl ketone were found to not cleave and did not operate in the present process. Diacetone alcohol appears to undergo a dehydration to produce water and mesityl oxide. Since water is present (Eq. 1) the adduct formed is hydrolyzed to produce the starting primary amine and acetone, hence for the purposes of this invention diacetone alcohol is not desirable.

EXAMPLE 4

Twenty ml of a mixture of n-amyl amine and piperidine (60:40 mol ratio) is added to the apparatus of Example 1. A molar excess of mesityl oxide (5 ml) is added and the reaction carried on for approximately 45 minutes at a pot temperature between 45° and 125° C. and over head temperature of 30° C. to 70° C. during this time. Approximately 0.23 moles of acetone is produced, leaving the adduct:

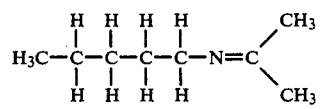

and piperidine. The piperidine is distilled from the residual mixture in high purity (99+%).

The residual adduct is hydrolyzed by adding 25 ml of water thereto, fractionated to recover acetone, and the water/n-amyl amine solution recovered. The water and/or n-amyl amine may be distilled to separate them from any unreacted mesityl oxide.

The invention claimed is:

1. A method for separating primary and secondary amines comprising contacting a mixture of primary and secondary amines with mesityl oxide, reacting said primary amine and mesityl oxide to produce a high boiling adduct thereof and acetone, removing acetone from said reaction, and separating said secondary amine from said high boiling adduct.

2. The method according to claim 1 wherein said primary amine has the structure R—NH$_2$ wherein R is a hydrocarbon radical having 1 to 30 carbon atoms.

3. The method according to claim 2 wherein said R is aliphatic, olefinic or aromatic.

4. The method according to claim 1 wherein said contacting is at a temperature above the boiling point of acetone.

5. The method according to claim 1 wherein said primary amine is n-amyl amine.

6. The method according to claim 5 wherein said secondary amine is piperidine.

7. The method according to claim 1 wherein said secondary amine has a lower boiling point than said adduct and is separated therefrom by fractionation.

8. The method according to claim 1 wherein said primary amine adduct is contacted with water whereby said adduct is hydrolyzed to produce said primary amine and acetone.

9. The process according to claim 8 wherein acetone is separated and recovered.

* * * * *